United States Patent
Cortez, Jr. et al.

(10) Patent No.: US 11,077,279 B2
(45) Date of Patent: Aug. 3, 2021

(54) HIGH FLOW THERAPY WITH BUILT-IN OXYGEN CONCENTRATOR

(71) Applicant: Vapotherm, Inc., Exeter, NH (US)

(72) Inventors: Felino V. Cortez, Jr., Bowie, MD (US); Charles Busey, Easton, MD (US); George C. Dungan, II, Dallas, TX (US)

(73) Assignee: Vapotherm, Inc., Exeter, NH (US)

( * ) Notice: Subject to any disclaimer, the term of this patent is extended or adjusted under 35 U.S.C. 154(b) by 1071 days.

(21) Appl. No.: 15/251,185

(22) Filed: Aug. 30, 2016

(65) Prior Publication Data

US 2017/0056613 A1    Mar. 2, 2017

Related U.S. Application Data

(60) Provisional application No. 62/212,365, filed on Aug. 31, 2015.

(51) Int. Cl.
*A61M 16/16* (2006.01)
*A61M 16/10* (2006.01)
(Continued)

(52) U.S. Cl.
CPC ............ *A61M 16/16* (2013.01); *A61M 16/00* (2013.01); *A61M 16/0063* (2014.02);
(Continued)

(58) Field of Classification Search
CPC .............. A61M 16/00; A61M 16/0063; A61M 16/0672; A61M 16/10; A61M 16/101;
(Continued)

(56) References Cited

U.S. PATENT DOCUMENTS

| | | | | |
|---|---|---|---|---|
| 4,072,148 A | * | 2/1978 | Munson | A61M 16/12 128/205.11 |
| 4,381,267 A | * | 4/1983 | Jackson | A61M 16/16 128/204.13 |

(Continued)

FOREIGN PATENT DOCUMENTS

| | | |
|---|---|---|
| EP | 1586345 A1 | 6/2015 |
| WO | WO-2008/030592 A2 | 3/2008 |
| WO | WO-2009/045198 A1 | 4/2009 |

OTHER PUBLICATIONS

International Search Report dated Oct. 11, 2016, International Application No. PCT/US2016/049417 (11 pages).

*Primary Examiner* — Tu A Vo
(74) *Attorney, Agent, or Firm* — White & Case LLP

(57) ABSTRACT

Apparatus and methods for delivering a heated and humidified mixture of oxygen and air are provided. The apparatus includes an air compressor and oxygen concentrator enclosed in the housing of a vapor transfer system. The air compressor supplies air at a first pressure to a gas inlet. The oxygen concentrator provides oxygen at a second pressure to the gas inlet. The oxygen concentrator and the air compressor are in fluid communication and are configured such that the first pressure of the compressed air and the second pressure of the oxygen are about equal. The apparatus includes a vapor transfer system having a gas passage, a liquid passage having heated liquid and vapor, and a membrane that separates the gas passage and liquid passage. The membrane is positioned to transfer vapor from the liquid passage to the gas passage.

23 Claims, 5 Drawing Sheets

(51) Int. Cl.
*A61M 16/00* (2006.01)
*A61M 16/06* (2006.01)
*A61M 16/12* (2006.01)

(52) U.S. Cl.
CPC ........ *A61M 16/0672* (2014.02); *A61M 16/10* (2013.01); *A61M 16/101* (2014.02); *A61M 16/109* (2014.02); *A61M 16/125* (2014.02); *A61M 2202/0208* (2013.01); *A61M 2205/42* (2013.01); *A61M 2210/1025* (2013.01)

(58) Field of Classification Search
CPC .. A61M 16/109; A61M 16/125; A61M 16/16; A61M 2205/42; A61M 16/0057; A61M 16/1005; A61M 2016/102; A61M 2016/1025; A61M 16/1045; A61M 16/1075; A61M 16/108; A61M 16/1085; A61M 16/12
See application file for complete search history.

(56) References Cited

U.S. PATENT DOCUMENTS

| | | | | |
|---|---|---|---|---|
| 5,954,050 A * | 9/1999 | Christopher | ...... | A61M 16/0465 128/204.23 |
| 7,476,212 B2 * | 1/2009 | Spearman | ........... | A61M 13/003 604/23 |
| 2001/0054422 A1 * | 12/2001 | Smith | ............... | A61M 16/0833 128/200.24 |
| 2005/0072426 A1 * | 4/2005 | Deane | ................... | A61M 16/10 128/204.26 |
| 2007/0246049 A1 * | 10/2007 | Takeda | ................ | A61M 16/101 128/205.27 |
| 2008/0118373 A1 * | 5/2008 | Richey | ................... | A61M 16/10 417/254 |
| 2008/0178880 A1 * | 7/2008 | Christopher | ....... | A61M 16/0875 128/204.23 |
| 2009/0107500 A1 * | 4/2009 | Edwards | ............. | A61M 16/101 128/204.23 |
| 2010/0059053 A1 | 3/2010 | Niland | | |
| 2010/0071698 A1 * | 3/2010 | Kiritake | ............... | B01D 53/047 128/205.27 |
| 2010/0242734 A1 * | 9/2010 | Maeda | ................... | A61M 16/10 96/110 |
| 2010/0307496 A1 * | 12/2010 | Lueckenhoff | ...... | A61M 16/0875 128/204.18 |
| 2012/0291779 A1 * | 11/2012 | Haartsen | ........... | A61M 15/0065 128/203.12 |
| 2012/0291884 A1 * | 11/2012 | Yamaura | ............ | B01D 53/0454 137/455 |
| 2013/0129541 A1 * | 5/2013 | Flanary | ............. | A61M 16/1075 417/420 |
| 2014/0165830 A1 * | 6/2014 | Dolensky | ................ | A62B 21/00 95/96 |
| 2014/0299129 A1 * | 10/2014 | Flanagan | ............. | A61M 16/10 128/203.22 |
| 2014/0318535 A1 * | 10/2014 | Bullock | ................ | A61M 16/16 128/202.15 |
| 2015/0144136 A1 * | 5/2015 | Niland | ................ | A61M 16/026 128/203.14 |

* cited by examiner

HIGH FLOW THERAPY WITH BUILT-IN OXYGEN CONCENTRATOR

CROSS-REFERENCE TO RELATED APPLICATIONS

This application claims the benefit of U.S. Provisional Application No. 62/212,365, filed on Aug. 31, 2015, which is hereby incorporated herein by reference in its entirety.

TECHNICAL FIELD

The present disclosure relates to systems for providing respiratory therapies. More specifically, the present disclosure relates to a system which provides heated and humidified oxygen and air mixtures.

BACKGROUND

Patients with respiratory ailments may be treated with respiratory assist devices that deliver supplemental breathing gas. Such devices may deliver gas to a patient using high flow therapy ("HFT"). During HFT therapy, breathing gas with a high flow rate is delivered to a patient via a nasal cannula in order to increase a patient's fraction of inspired oxygen (FiO2) while decreasing a patient's work of breathing. In some implementations, HFT devices heat and humidify the delivered breathing gas to reduce patient discomfort.

Patients with respiratory ailments may also benefit from oxygen therapy. During administration of oxygen therapy, oxygen, or breathing gas including oxygen, is delivered to the patient. While HFT and oxygen therapy have similarities, patients receiving HFT and oxygen therapy must receive one therapy at a time due to differing device requirements. By applying the therapies individually, the amount of the patient's time consumed by therapy is increased, inevitably increasing the discomfort a patient experiences during therapy and preventing the patient from enjoying other activities.

Further burdening patients is the lack of adequate at-home HFT therapies as patients with respiratory ailments may find high-pressure breathing gas unavailable in the home setting. Instead, patients are forced to travel to clinical settings with high-pressure breathing gas sources.

SUMMARY

Disclosed herein are systems, methods, and devices for a self-contained apparatus capable of delivering a heated and humidified mixture of oxygen and air to a patient in order to overcome the aforementioned problems. Furthermore, these systems, methods and devices allow for delivery of heated and humidified breathing gas mixtures to a patient in a home environment, relieving a patient from the burden of having to travel to a clinic. This, and other advantages described below, is achieved by incorporating a vapor transfer system with an air compressor and an oxygen concentrator. The incorporation of an HFT system which incorporates both a compressed air source and an economical means of producing medical-grade oxygen allows for broad deployment of HFT in non-clinical settings. Traditionally, oxygen concentrators have not been used in traditional medical-grade HFT systems due to the low pressure output of these concentrators.

The system described herein overcomes the challenges associated with the administration of HFT in non-clinical settings by incorporating an HFT system with an air compressor and an oxygen concentrator which operate at low pressures. The system incorporates these features into a single portable housing which minimizes clutter in a non-clinical or home environment and maximizes patient mobility around the system. The air compressor acts as a source for pressurized air and the oxygen concentrator provides oxygen for blending into a breathing gas mixture having an appropriate concentration of oxygen. The oxygen and the air are pressure-matched to facilitate mixing before being heated and humidified for delivery to the patient. The system allows the low pressure gas from the oxygen concentrator to blend with a low pressure gas from an air compressor. The matched pressures allow the system to blend the air-oxygen breathing gas having higher concentrations of oxygen and with higher output gas flow before it is directed to the HFT system. Following the heating and humidifying of the gas, the system incorporates low resistance large inner diameter tubing to allow for high gas flow of up to 40 liters per minute (lpm) to be delivered to the patient via a nasal cannula. Use of a compressor and an oxygen concentrator to provide gas and oxygen which is mixed, heated, and humidified allows for administration of HFT therapies in home and other non-clinical environments without the need for additional equipment such as oxygen cylinders, tanks, or high-pressure sources.

Furthermore, the system provides a means for efficient administration of HFT while maximizing patient comfort. In some implementations, the system provides high flow of breathing gas through tubing with a large inner diameter delivered to a nasal cannula with small inner diameter nasal prongs. Due to challenges associated with the condensation of heated and humidified breathing gas when transported through long lengths of tubing, lengths of tubing of about 2 m are used with HFT. The system is designed for use with a variety of cannula configurations. One such configuration minimizes the amount of noise that reaches a patient by maintaining fluid separation of the flows of gas to each nare from the vapor transfer unit to the nare. Another possible configuration of the nasal cannula includes a point of fluid communication at the point of the administration of the gas via the nasal prongs into the nares. Noise reduction to the patient is further decreased by use of large diameter tubing. The system utilizes dual low pressure compressor and concentrator systems which further decrease device noise.

Moreover, the system is able to provide both heated and humidified HFT and oxygen therapy delivering humidified but non-heated breathing gas with a high concentration of oxygen to a patient. Because the high-concentration oxygen breathing gas is not humidified, issues of rainout and condensation present less of a challenge and the high concentration oxygen breathing gas can be provided to a patient through a long length of tubing, allowing maximized patient mobility while receiving oxygen therapy. By combining the HFT and oxygen therapy in one self-contained system, the total amount of time consumed by administering respiratory therapy to a patient is reduced, and the need for additional devices in a home environment is eliminated.

In one aspect, an apparatus for delivering a heated and humidified mixture of oxygen and air includes a vapor transfer system that has a housing, a gas inlet, a gas outlet, a liquid inlet, a liquid outlet, a gas passage coupling the gas inlet to the gas outlet, a liquid passage coupling the liquid inlet to the liquid outlet, and a membrane that separates the gas passage and liquid passage. The membrane is positioned to transfer vapor from the liquid passage to the gas passage. The apparatus also includes a liquid supply coupled to the liquid inlet, and the liquid supply also has a heater that heats liquid of the liquid supply. The apparatus also includes an air compressor enclosed in the housing of the vapor transfer system. The air compressor is configured to supply air at a first pressure to the gas inlet. Additionally, the apparatus includes an oxygen concentrator also enclosed in the housing of the vapor transfer system. The oxygen concentrator is configured to output oxygen at a second pressure to the gas inlet. The oxygen concentrator and the air compressor are in fluid communication and are configured such that the first pressure of the compressed air and the second pressure of the oxygen are about equal.

The pressure of the compressed air and the pressure of the oxygen may vary. For example, in certain implementations, the first pressure of the compressed air and the second pressure of the oxygen are equal to within 10%. In some implementations, the first pressure of the compressed air and the second pressure of the oxygen are equal to within 5%. In some implementations, the first pressure of the compressed air and the second pressure of the oxygen are equal to about 6-11 psi.

In some implementations, the gas outlet is in fluid communication with a first elongated lumen and a second elongated lumen. The first elongated lumen is coupled to a first end of a nasal cannula and the second elongated lumen is coupled to a second end of a nasal cannula, and a first flow of gas from the first elongated lumen and a second flow of gas from the second elongated lumen are directed through a first and second nasal prong. In some implementations, the first flow of gas through the first elongated lumen and the second flow of gas through the second elongated lumen are not in fluid communication through the nasal cannula. In some implementations, the first flow of gas through the first elongated lumen and the second flow of gas through the second elongated lumen are in fluid communication at the first and second nasal prong. In some implementations, the nasal cannula defines a constant diameter flow path for the first and second flows of gas. In some implementations, the inner diameter of the first elongated lumen and the inner diameter of the second elongated lumen are about equal to ¼". In some implementations, the flow rate through the first elongated lumen and the second elongated lumen is equal to 40 lpm or greater.

In some implementations, the apparatus also includes a base unit that releasably engages the vapor transfer unit to enable reuse of the base unit and selective disposal of the vapor transfer unit. The liquid passage is coupled to the base unit to provide liquid flow between the base unit and a vapor transfer unit when the vapor transfer unit is received by the base unit.

In some implementations, the first elongated lumen and the second elongated lumen each has a length of about 1.8 meters and the lumens each provide gas from the gas outlet at a flow rate of about 5-40 (lpm). In certain implementations, the first elongated lumen and the second elongated lumen each has a length of about 10 meters. In some implementations, the first elongated lumen and the second elongated lumen provide a gas from the gas outlet at a range of flow rates of about 0.25-10 lpm.

In some implementations, the first flow of gas from the first elongated lumen and the second flow of gas from the second elongated lumen maintain a temperature of within 5 degrees Celsius from a set temperature across a range of flow rates from 5-40 lpm. In some implementations, a flow of gas exits the gas outlet with a humidity within the range of 26-56 mg/L.

In some implementations, the membrane in the vapor transfer system comprises a plurality of hollow fiber tubes. In some implementations, the gas passage of the vapor transfer system is enveloped by the liquid passage. In some implementations, the liquid passage is enveloped by the gas passage. In some implementations, the apparatus operates at a sound level of about 55 dB or lower.

BRIEF DESCRIPTION OF THE DRAWINGS

The foregoing and other objects and advantages will be apparent upon consideration of the following detailed description, taken in conjunction with the accompanying drawings. The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Aspects of the apparatus will now be described with reference to the figures. Such figures are intended to be illustrative rather than limiting and are included herewith to facilitate the explanation of the present invention.

The systems, devices and methods described herein provide a means for producing and delivering a heated and humidified mixture of oxygen and air to a patient without use of external high flow oxygen and air sources. The systems, devices, and methods described herein provide for HFT use in a home or other non-clinical setting. Making use of an air compressor, an oxygen concentrator and vapor transfer system, pressurized air and concentrated oxygen may be produced and mixed to achieve oxygen-air mixtures which are heated and humidified for patient delivery. Matching the pressure of the compressed air and concentrated oxygen allows for mixing of oxygen-air blends of varying oxygen concentration at a variety of flow rates.

Figure 1:
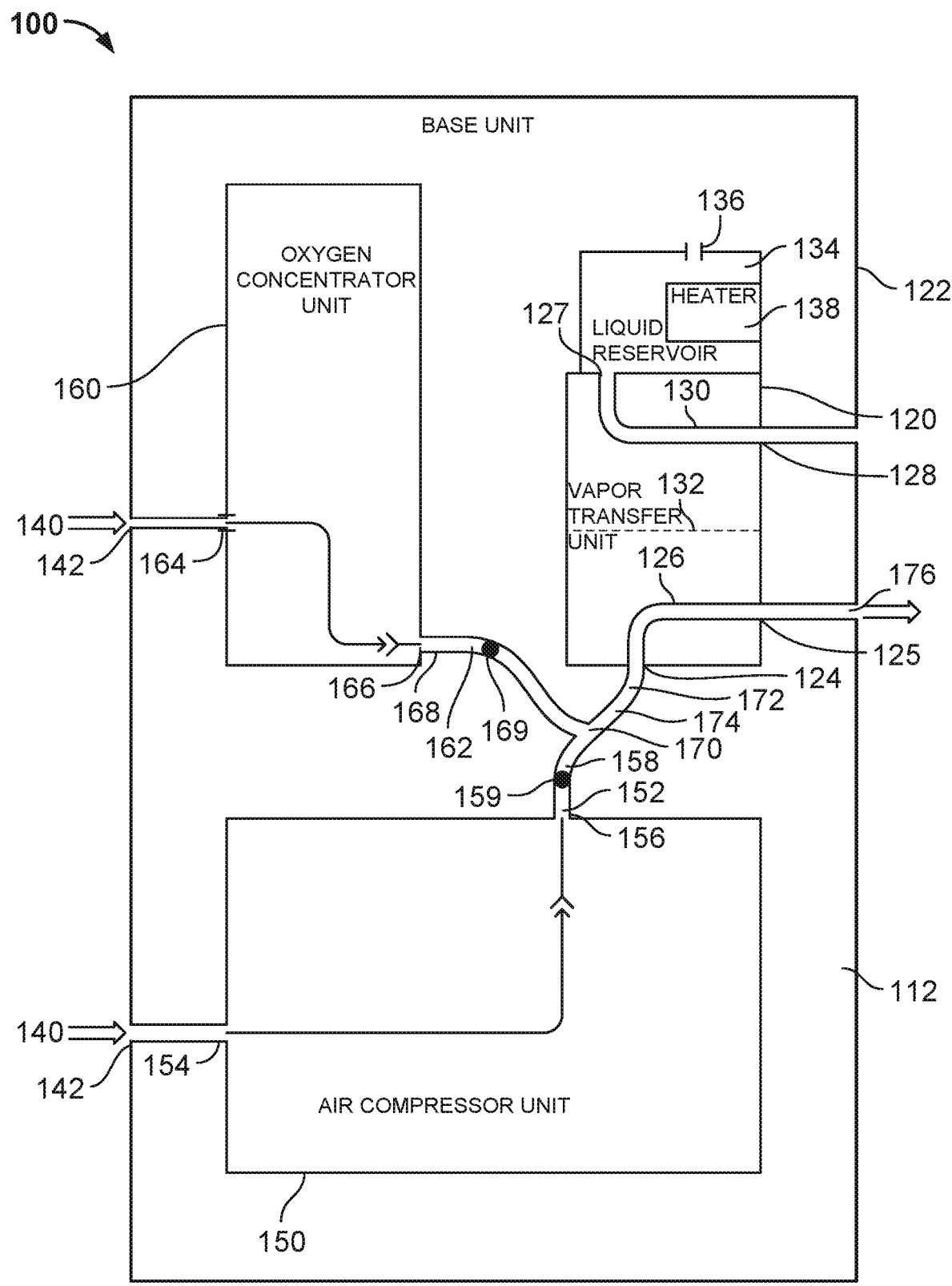
FIG. 1 shows a schematic representation of a system for delivering a heated and humidified mixture of oxygen and air according to an exemplary aspect of this invention.

FIG. 1 shows a schematic representation of a system for delivering a heated and humidified mixture of oxygen and air. The system 100 includes a base unit 112, a vapor transfer unit 120, an air compressor unit 150 and an oxygen concentrator unit 160. The base unit 112 may include controls for operating the system 100 and for controlling the vapor transfer unit 120, air compressor unit 150 and oxygen concentrator unit 160 individually. The vapor transfer unit 120 includes a housing 122, a gas inlet 124, a gas outlet 125, a liquid inlet 127, a liquid outlet 128, a gas passage 126, a liquid passage 130, a membrane 132, a liquid reservoir 134, a liquid port 136, and a heater 138. The system is configured to draw in air 140 through an air inlet 142 in the housing 122, and to direct the air 140 to the air inlet 154 in the air compressor unit 150 or to the air inlet 164 in the oxygen concentrator unit 160. In some implementations there may be a single air inlet 142 in the housing 122 which draws in air 140 and directs the air 140 to both the air compressor unit 150 and the oxygen concentrator unit 160. In other implementations there may be multiple air inlets 142 in the housing 122. The air compressor unit 150 pressurizes the air 140 and expels the compressed air 152 through a compressed air outlet 156 into a compressed air passage 158. The air is expelled having a first pressure 159. The oxygen concentrator unit 160 concentrates the oxygen 162 from the air 140 and expels the concentrated oxygen 162 from the oxygen concentrator unit 160 through an oxygen outlet 166 and into an oxygen passage 168. The oxygen 162 exits the concentrator unit 160 with a second pressure 169. The first pressure 159 output from the air compressor unit 150 is matched to the second pressure 169 output from the oxygen concentrator unit 160. The matched pressures allows the air and oxygen to blend at a higher oxygen concentration and at high output gas flow without one gas overcoming the other.

The compressed air passage 158 and the oxygen passage 168 meet at a junction 170 in the internal tubing where the flows are in fluid communication. The compressed air 152 and concentrated oxygen 162 gases are blended at the junction 170 to form an oxygen-air breathing gas mixture 174 and continue through the gas passage 172 to the gas inlet 124 into the vapor transfer unit 120. In some implementations, blending of the gases (air 152 and oxygen 162) may be aided by a manifold or deflector which directs the gases in a direction. The first pressure 159 of the compressed air 152 may be matched to the second pressure 169 of the concentrated oxygen 162 to allow mixing at high oxygen concentrations. The first pressure 159 and the second pressure 169 may be controlled by controls on the base unit 112 or they may be automatically controlled to maintain a pressure match. The first pressure 159 and the second pressure 169 may be controlled to be about 6 psi. In some implementations the first pressure 159 and the second pressure 169 are maintained at 5-11 psi. A pressure of 5-11 psi is attainable for a self-contained oxygen concentrator and air compressor and does not require the use of high-pressure gas sources. These pressures allow the system to be used in a home or non-clinical environment with minimized noise output. The first pressure 159 may be controlled to be equal to the second pressure 169 to within a percentage (e.g. within 25%, 20%, 10%, 5% 3%). Closely matched pressures avoids backflow and prevents one mixed gas from overcoming the other during mixing. Blending gases with matched pressures allows for the mixing of the desired concentration of oxygen.

The vapor transfer unit 120 is configured to heat and humidify the oxygen-air breathing gas mixture 174. The vapor transfer unit 120 includes a gas passage 126 which connects the gas inlet 124 to a gas outlet 125. The vapor transfer unit 120 also includes a liquid reservoir 134 which may be filled at a liquid port 136. Liquid may leave the liquid reservoir 134 and enter the vapor transport unit 120 at a liquid inlet 127 connected to a liquid outlet 128 via a liquid passage 130. The liquid reservoir 134 further includes a heater 138 which is configured to heat the liquid and may be controlled by control on the base unit 112. The heater 138 heats the liquid and the liquid is transported through the liquid passage 130 to the vapor transfer unit 120 where vapor from the heated liquid may be transferred to the oxygen-air breathing gas mixture 174 through a membrane 132 which separates the liquid passage 130 and the gas passage 172.

After passing through the gas passage 126 the mixture of heated and humidified oxygen-air breathing gas mixture 174 passes out of the housing 122 of the vapor transfer unit at a gas outlet 176. The gas outlet 176 is configured to be connected to a variety of possible cannulas or other mechanisms for delivery of gas to a patient.

In some implementations the vapor transfer unit 120 may be configured to be releasably coupled to the base unit 112 such that the vapor transfer unit 120 may be disposable while the base unit 112 may be reused. A releasable vapor transfer unit 120 may additionally be removed for cleaning or maintenance. In such implementations, the liquid passage 130 may be coupled to the base unit 112 to allow liquid flow between the base unit 112 and the vapor transfer unit 120 when the vapor transfer unit 120 is releasably coupled to the base unit 112.

The membrane 132 of the vapor transfer unit 120 may be comprised of a plurality of hollow fibers. Furthermore, in some implementations the membrane 132 may separate the gas passage 126 from the liquid passage 130 such that the gas passage 126 is enveloped by the liquid passage 130. In other implementations the gas passage 126 and the liquid passage 130 may be arranged such that the gas passage 126 envelopes the liquid passage 130.

The vapor transfer unit 120 is configured to heat and humidify the oxygen-air breathing gas mixture 174 before delivery to a patient. The temperature of the heater 138 may be controllable by an operator using controls on the base unit 112. The temperature range may alternatively be preset or constrained to an allowable range of temperatures (e.g. 33-41° C.). Temperatures in the range of 33-41° C. are comfortable for a patient and allow a gas humidity to be maintained over the delivery path to a patient with minimal condensation and rainout. The temperature control of the oxygen-air breathing gas mixture 174 may be controllable such that for a variety of flow rates the set temperature is maintained within an average amount (e.g. within 2° C., 5° C., 10° C.). The humidity of the oxygen-air breathing gas mixture 174 may also be controlled such that humidity of up to 90-100% at room temperature is achieved (e.g. 35-56 mg/L). In some implementations, a humidity of about 22-56 mg/L may be provided.

Figure 2:
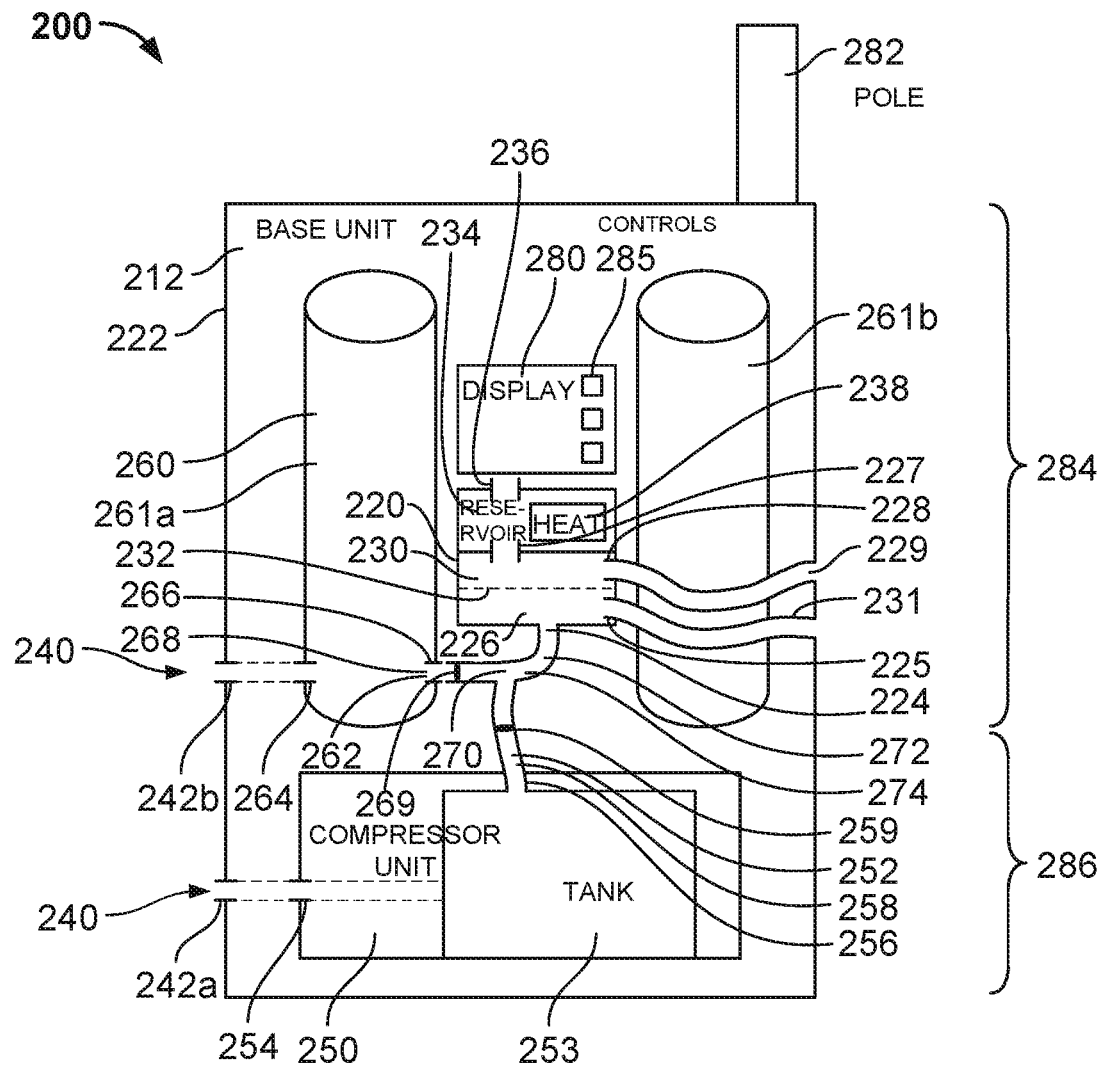
FIG. 2 is a front perspective view of an exemplary embodiment of the system.
Figure 3:
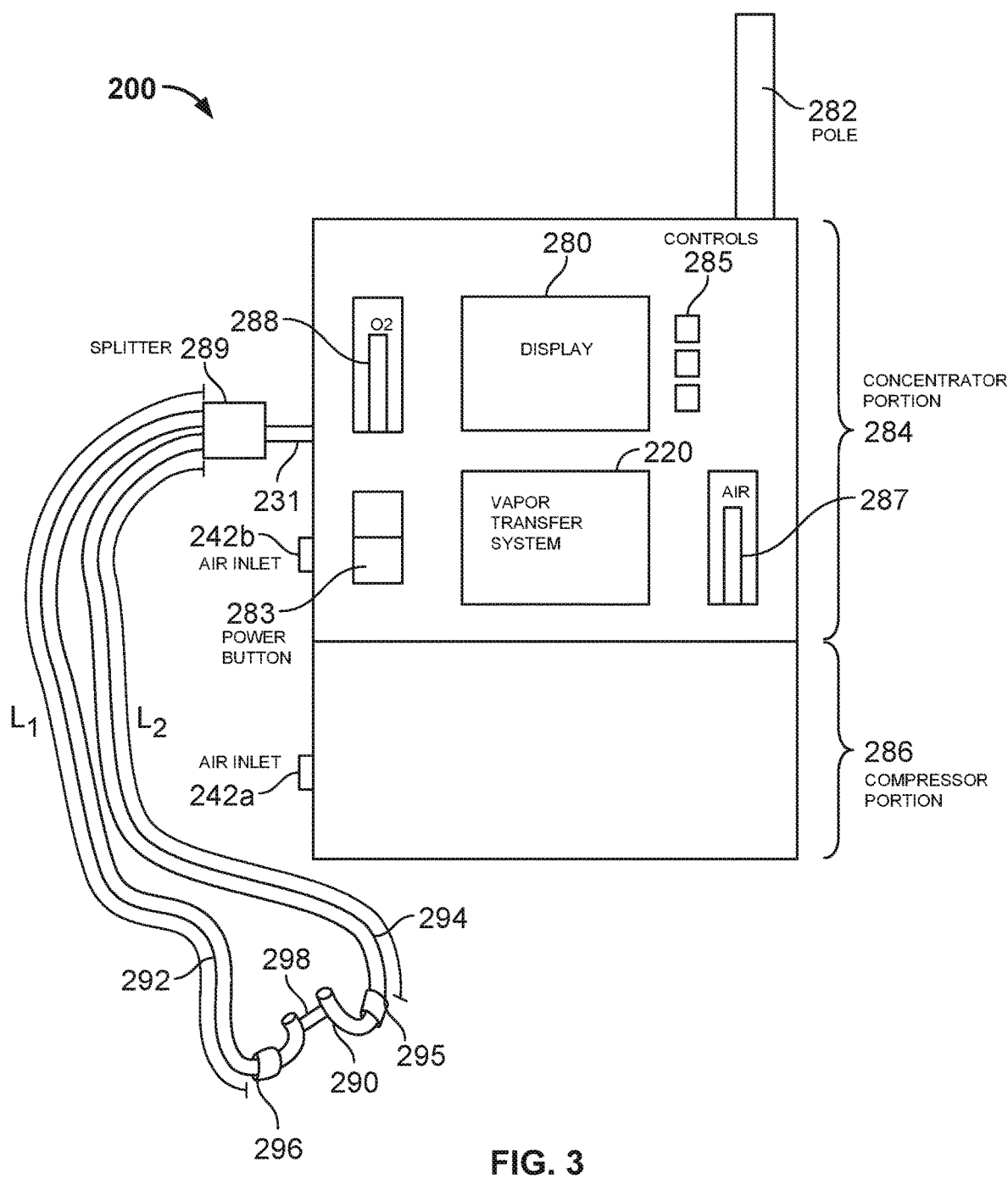
FIG. 3 is a front perspective view of the exterior of an exemplary embodiment of the system.

FIGS. 2 and 3 show perspective views of an exemplary embodiment of the system. Specifically, FIG. 2 shows a front perspective view of an exemplary embodiment of the system, while FIG. 3 shows a front perspective view of the exterior of an exemplary embodiment of the system. The system 200 has a compressor portion 286 and a concentrator portion 284 which also includes the vapor transfer system 220. The system 200 includes a compressor unit 250 having an air inlet 254 and a compressed air outlet 256, an oxygen concentrator unit 260 having an air inlet 264 and a compressed oxygen outlet 266, a compressed air passage 258, an oxygen passage 268, a junction where the compressed air and concentrated oxygen meet and mix at junction 270, and a vapor transfer system 220 comprising a housing 222, a gas inlet 224, a gas outlet 225, a gas passage 226 connecting the gas inlet 224 and gas outlet 225, a liquid reservoir 234, a liquid inlet 227, a liquid outlet 228, a liquid passage 230, a heater 238 and a membrane 232 to separate the liquid passage 230 and the gas passage 226. The vapor transfer system 220, air compressor unit 250, and oxygen concentrator unit 260 are all contained within the vapor transfer system 220 housing 222. The system 200 is thus self-contained and portable, allowing broad deployment of HFT into the home or non-clinical environment while limiting clutter.

The system 200 intakes air 240 at an air inlet 242a and 242b. Though two inlets are shown, the system may have a single air inlet 242a,b at which air is drawn in and directed to the air compressor unit 250 and to the oxygen concentrator unit 260. Air 240 is directed into the air compressor unit 250 through an inlet 254. The air compressor unit 250 pressurizes the air 240. The air compressor unit 250 may include a tank 253. Once pressurized, the compressed air 252 is directed out of the air compressor unit 250 at a compressed air outlet 256 and into a compressed air passage 258. The compressed air 252 in the compressed air passage 258 may have a first pressure 259. The pressure may be monitored.

The system 200 also directs air 240 into the oxygen concentrator unit 260 through the air inlet 264. The oxygen concentrator unit 260 is shown having two cylinders 261a and 261b. The oxygen concentrator unit 260 may use pressure swing adsorption technology making use of adsorptive materials including zeolites, activated carbon, membrane separation of oxygen or molecular sieves to concentrate oxygen 262 from ambient air 240. The concentrated oxygen 262 is directed out of the oxygen concentrator unit 260 through a concentrated oxygen outlet 266 and into an oxygen passage 268. The concentrated oxygen outlet 266 in the passage has a second pressure 269. The oxygen passage 268 is in fluid communication with the compressed air passage 258 at a junction 270. The first pressure 259 of the compressed air 252 is matched to the second pressure 269 of the concentrated oxygen 262. The matched pressures may be equal or may be matched to within a percentage (e.g. to within 2%, 5%, 7%, 10%, 15%). Matching the first pressure 259 of the compressed air 252 and the second pressure 269 of the concentrated oxygen 262 before mixing results in a smoother blending process. The mixing of the compressed air 252 and concentrated oxygen 262 may also be aided by the use of a manifold or directing device at the junction 270 to direct the flows in a single direction. The blending of concentrated oxygen 262 with compressed air 252 at a matched pressure allows mixing of an oxygen-air breathing gas mixture 274 having an appropriate concentration of oxygen for therapeutic use.

The oxygen-air breathing gas mixture 274 continues through a gas passage 272 and into a vapor transfer system 220 through a gas inlet 224 leading to a gas passage 226 through the vapor transfer system 220. The vapor transfer system 220 also includes a liquid reservoir 234 which is Tillable with a liquid such as water through the liquid port 236. The liquid reservoir 234 includes a heater 238 which heats the liquid and produces a vapor. The vapor transfer system 220 also includes a liquid inlet 227 through which liquid leaves the liquid reservoir 234 and enters the liquid passage 230 and a liquid outlet 228 from the vapor transfer system 220. The gas passage 226 is separated from the liquid passage 230 by a membrane 232 which allows the transfer of vapor from the liquid passage 230 to the gas passage 226.

In some implementations the membrane 232 may be composed of a plurality of hollow fibers. In some implementations the gas passage 226 may be enveloped by the liquid passage 230. In other implementations the liquid passage 230 may be enveloped by the gas passage 226. The transfer of vapor to the oxygen-air breathing gas mixture 274 in the gas passage 272 allows the oxygen-air breathing gas mixture 274 to become heated and humidified before delivery to a patient.

The gas passage 226 directs the heated and humidified oxygen-air breathing gas mixture 274 out of the vapor transfer system 220 at a gas outlet 225. The heated and humidified oxygen-air breathing gas mixture 274 may be further directed out of the housing 222 through a housing gas outlet 276 for delivery to a patient. The liquid in the liquid passage 230 may also be directed out of the vapor transfer system 220 at a liquid outlet 228. The liquid may be further directed out of the housing at a housing liquid outlet 229 for collection.

Various aspects of the system 200 may be controlled by controls 285 on a user display panel 280. The user may have controls which adjust parameters including the temperature and humidity of the oxygen-air breathing gas mixture 274. In some implementations, the gas temperature may be adjustable between ambient room temperature up to 43° C., with humidity levels adjustable between 90 and 100%. The controls may also adjust the flow rate of the oxygen-air mixture and the ratio of the mixture of oxygen and air in the heated and humidified oxygen-air breathing gas mixture 274. In some implementations the system 200 may deliver a continuous flow of heated and humidified oxygen-air breathing gas mixture 274 at flow rates of 1-40 lpm. The oxygen admixture to the flow may be varied between 0 lpm and 20 lpm. A power button may be incorporated 283, as well as a flow meter displaying the flow rate of the concentrated oxygen 288 and a flow meter displaying the flow rate of the compressed air 287. The system 200 may be further adapted by the addition of an IV pole 282. The system 200 is self-contained and does not require use of external gas sources, though they may be used. Additionally, the use of a low pressure oxygen concentrator and a low pressure air compressor allows the apparatus to operate at a sound level of 55 dB or lower.

In some implementations, the system 200 may be configured to allow for the vapor transfer system 220 to be detachable from the base unit 212. This allows for disposal of the vapor transfer system 220 and reuse of the base unit 112. This further allows for removal of the vapor transfer system for cleaning, inspection or maintenance. In some implementations, the liquid passage 230 is coupled to the base unit 212 for liquid flow between the base unit 212 and the vapor transfer system 220 when the vapor transfer system is received by the base unit.

The heated and humidified oxygen-air breathing gas mixture 274 exits the housing 222 at a housing gas outlet 231. The heated and humidified oxygen-air breathing gas mixture 274 may be routed to the patient by a gas splitter 289 which directs the gas to a first elongated lumen 292 having a first length L1 and a second elongated lumen 294 having a second length L2. The first elongated lumen 292 may be coupled the first end 296 of a nasal cannula 290. The second elongated lumen 294 may be coupled to a second end 295 of the nasal cannula 290. The first elongated lumen 292 and the second elongated lumen 294 is each composed of large inner diameter, low-resistance tubing, allowing the oxygen-air breathing gas mixture to achieve a high flow rate for delivery to the patient. In some implementations, the first end 296 of the nasal cannula 290 and the second end 295 of the nasal cannula 290 may be connected by a bridging piece 298 which does not allow fluid communication between the two ends (296 and 295). Though a nasal cannula 290 is shown here having two nares not in fluidic communication and separated by a bridging element 298, any suitable nasal cannula or mask may be used to deliver the air-oxygen breathing gas mixture to the patient. In other implementations, the gas from the first elongated lumen 292 and the second elongated lumen 294 may be in fluid communication within the nasal cannula 290. In some implementations, the gas from the first elongated lumen 292 and the second elongated lumen 294 may be in fluid communication at the point of administration of the gas via the prongs of the nasal cannula 290 into the nose. In some implementations the flow of gas through the first elongated lumen 292 may not be in fluid communication with the flow of gas through the second elongated lumen 294 after leaving the gas splitter 289 until expulsion from the nasal cannula 290. In some implementations the nasal cannula defines a constant diameter flow path. In some implementations, the use of low resistance tubing with a large inner diameter throughout the system allows a gas flow output of up to 40 lpm. The use of tubing with a large inner diameter minimizes the backpressure within the system. In some implementations, the nasal cannula has a large inner diameter cross section at the supply tubing and the inlet port with nasal prongs having a small inner diameter. In some implementations an inner diameter of the first and second elongated lumens may be the same for both the first elongated lumen and the second elongated lumen and may be an inner diameter about equal to ¼" (e.g. ⅜", ¼", ⅝", ½"). The use of tubing having an inner diameter of about ¼" provides the breathing gas to the patient at a high flow rate. Additionally, the larger inner diameter tubing provides a favorable ratio of surface area to volume and has a decreased rate of condensation and rainout compared to smaller diameters of tubing. The Biot number associated with tubing with an inner diameter of about ¼" is large when compared to tubing with a smaller inner diameter which may suffer from greater heat transference and more condensation and rainout. In some implementations the flow rate through the first elongated lumen may be 40 lpm or greater. Though the delivery of the oxygen-air gas mixture is shown as through a split nasal cannula, the gas may be delivered by any suitable nasal cannula or patient interface including masks and tracheal adaptors.

In some implementations the system 200 may be configured to operate in two modes. A first mode may provide heated and humidified oxygen-air breathing gas mixture 274 to a patient as described. A second mode may provide a humidified but not heated oxygen-air breathing gas mixture 274 to a patient. In some implementations, the second mode allows for delivery of a high concentration of oxygen gas (e.g. 90-93% oxygen) at flow rates of 1-20 lpm in a humidified but non-heated gas through a long length of tubing. As the gas in the second mode is not heated, there is decreased occurrence of rain-out or condensation during delivery of the breathing gas through the length of tubing. The second mode may allow for use of first and second elongated lumens (292 and 294) of longer lengths, L1 and L2, respectively. A longer length of tubing allows a patient receiving oxygen therapy in their own home to be mobile while receiving the oxygen therapy. In some implementations, the system 200 can switch between the delivery of high concentration oxygen and delivery of HFT oxygen-air mixture having a controllable oxygen concentration of between 21-93% oxygen which may be flow rate dependent. Additionally, providing both oxygen therapy and HFT via a single system decreases the need for further equipment in the home environment and streamlines therapy. Thus in some implementations, L1 and L2 may be 1.8 meters or longer (e.g. 1.8 m, 2 m, 2.5 m, 3 m) and the first elongated lumen 292 and the second elongated lumen 294 may each provide gas at a flow rate of 5-40 lpm. Flow rates of 8-40 lpm are sufficient to provide the core benefits of HFT. Administration of HFT with these flow rates reduces the respiratory burden on a patient by warming and humidifying them and serves to flush the dead space from the nasal and pharyngeal cavities prior to inspiration. In some implementations, L1 and L2 may be about 10 m in length (e.g. 7 m, 8 m, 9 m, 10 m, 11 m, 15 m) and the first elongated lumen 292 and the second elongated lumen 294 may each provide gas at a flow rate of about 2 lpm. A flow rate of 2 lpm is typically sufficient to provide long term oxygen therapy to a patient. In some implementations, the first elongated lumen 292 and the second elongated lumen 294 may each provide gas at a flow rate of 0.25-10 lpm.

Figure 4:
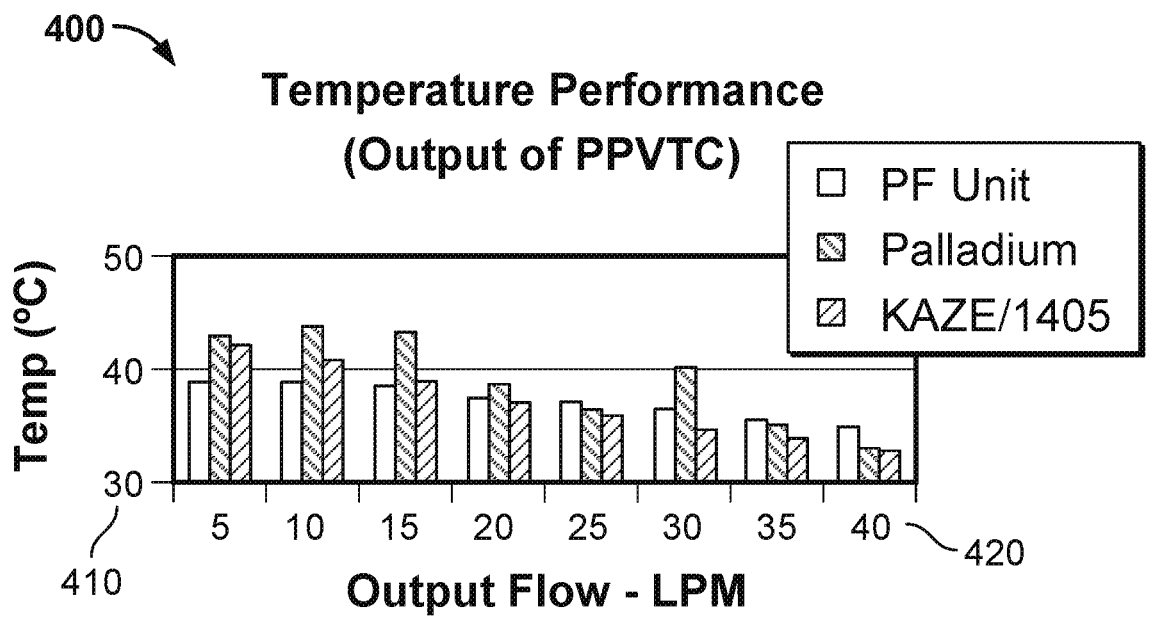
FIG. 4 is a histogram displaying temperature performance of the system over a variety of breathing gas output flow rates with comparison to other HFT devices.

FIG. 4 shows a histogram 400 displaying temperature performance of the system 100 over a variety of breathing gas output flow rates. The y-axis 410 represents the temperature of the oxygen and air mixture output by the system measured in degrees Celsius. The x-axis 420 represents the set flow rate of the oxygen and air mixture measured in lpm. The flow rate was varied from 5 lpm to 40 lpm in increments of 5 lpm. The temperature of the system was set to 37° C. and the temperature of the oxygen and air mixture output from the system 100 at the gas outlet was measured and recorded. The temperature performance of the system 100 is displayed with the temperature performance of two other HFT systems, the PF Unit and the Palladium. The histogram 400 shows that the system 100 performs similarly to the PF Unit over the range of flow rates tested. The histogram also shows that the system 100 maintains the set temperature within about 5° C. over the range of flow rates tested. The recorded temperature of the output oxygen and air mixture is about 42° C. at 5 lpm flow rate and is about 33° C. at 40 lpm flow rate. The system 100 is able to maintain a set temperature within about 5° C. over flow rates ranging from 5 lpm to 40 lpm.

Figure 5:
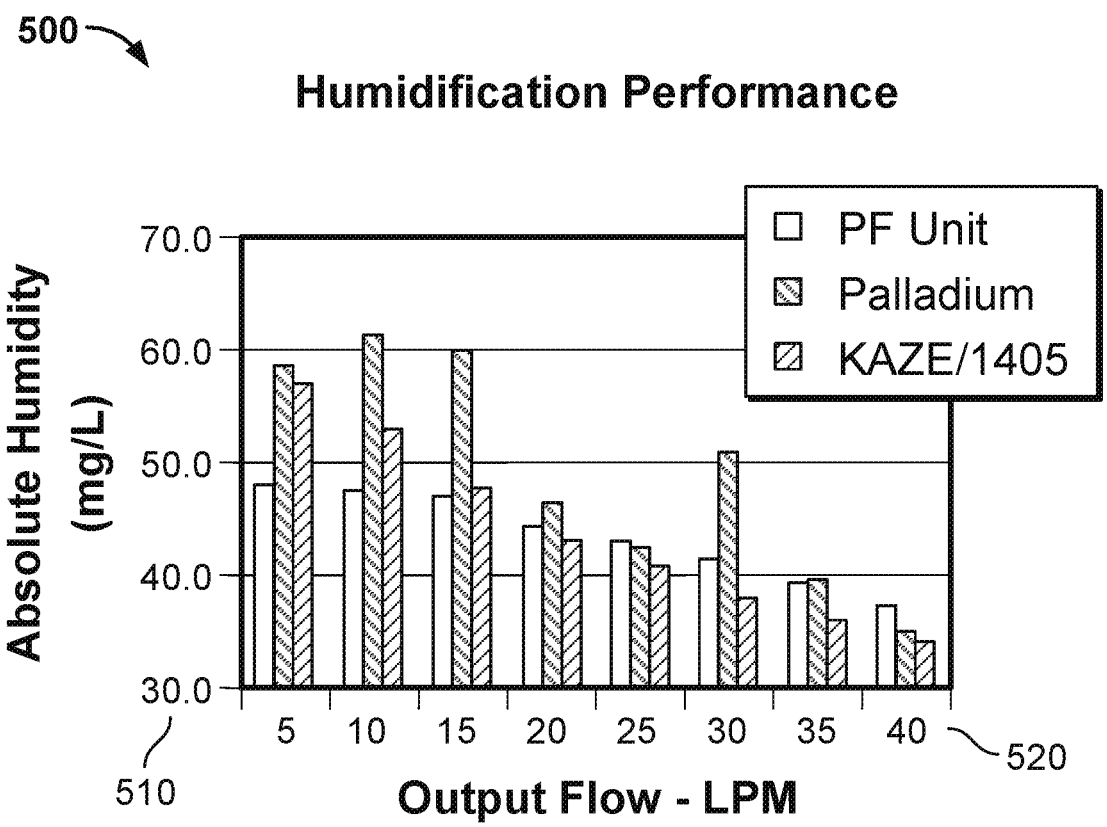
FIG. 5 is a histogram displaying humidification performance of the system over a variety of breathing gas output flow rates with comparison to other HFT devices.

FIG. 5 shows a histogram 500 displaying humidification performance of the system over a variety of breathing gas output flow rates. The x-axis 520 represents the set flow rate of the oxygen and air mixture output by the system 100 measured in lpm. The y-axis 510 represents the measured absolute humidity of the oxygen and air mixture in mg/l. The humidification performance of the system 100 is displayed with the humidification performance of two other HFT systems, the PF Unit and the Palladium. The flow rate was varied from 5 lpm to 40 lpm in increments of 5 lpm. The temperature of the system was set to 37° C. and the humidity of the oxygen and air mixture output from the system 100 at the gas outlet was measured and recorded for each of the input flow rates. The histogram 500 shows that the system 100 performs similarly to the PF Unit at all tested flow rates and performs similarly to the Palladium unit at flow rates of 20-40 lpm. The histogram shows that the system 100 provides absolute humidity levels of between 35 mg/L and 55 mg/L at 37° C. over flow rates of 5 lpm to 40 lpm.

Figure 6:
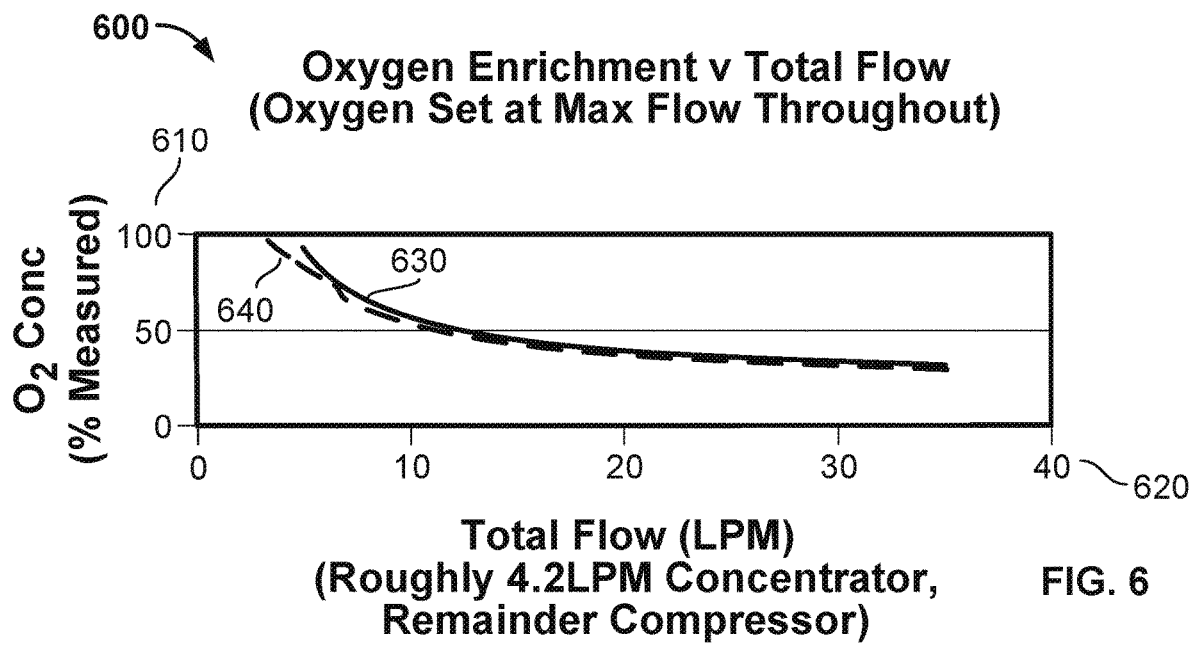
FIG. 6 is a graph displaying oxygen enrichment of the system over a variety of total output flow rates with comparison to other devices.

FIG. 6 shows a graph 600 displaying oxygen enrichment of the system over a variety of output flow rates. The x-axis 610 displays the total flow in lpm of the air oxygen mixture from the outlet. The oxygen concentrator unit 160 was set to its maximum flow rate of 5 lpm and the total flow is adjusted upward to increase the total flow of oxygen and air from the vapor transfer unit 120. The y-axis 620 displays the oxygen concentration as a percent measured at the output of the oxygen air mixture from the system 100. The oxygen enrichment of the system 100 is displayed with the oxygen enrichment of two other HFT systems, the PF Unit and the Palladium. The measured value is displayed as a line 630, while the theoretical value is also displayed as a dashed line 640. The theoretical performance is calculated as the optimal performance assuming the optimal concentrator oxygen fraction of 0.92. Though the concentrator was set to its maximum output flow of 5 lpm, the concentrator did not generate a flow rate of 5 lpm, but rather 4.2 lpm of flow. The graph shows that the oxygen enrichment performance of the system 100 is similar to the theoretical optimal performance.

Figure 7:
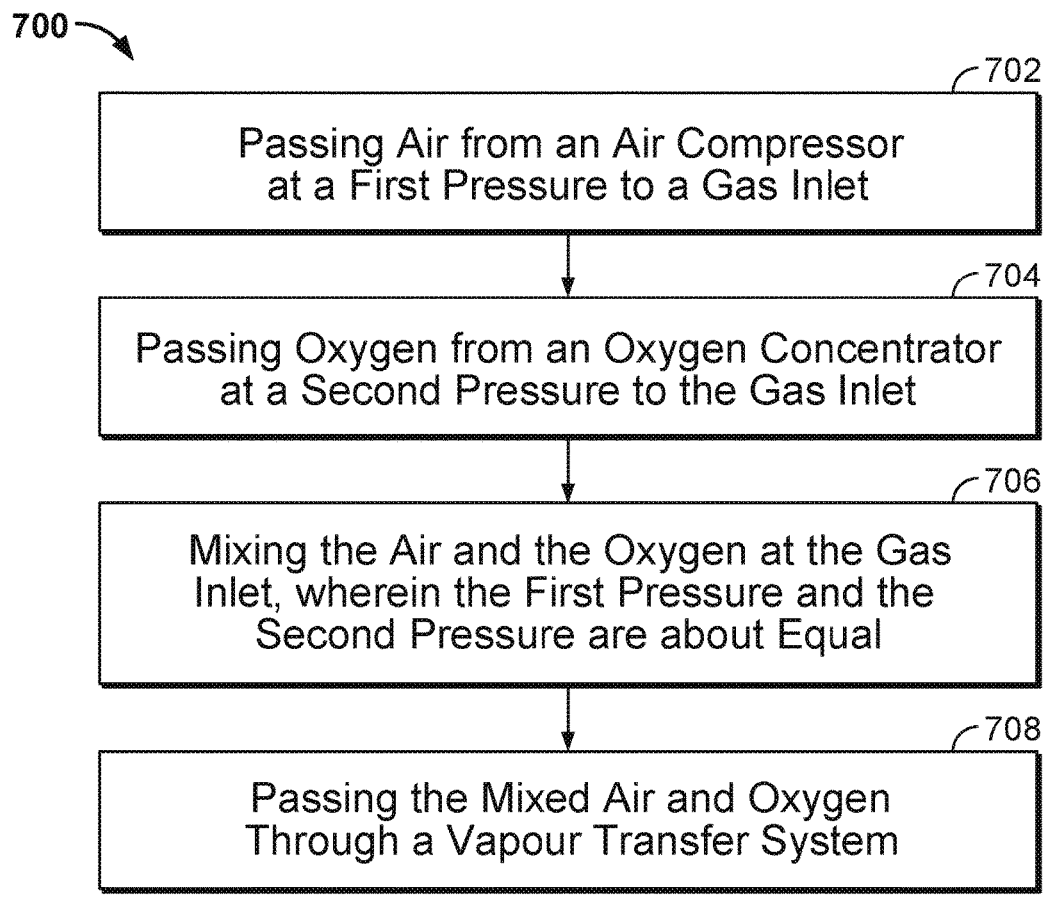
FIG. 7 is an illustrative process for achieving a heated and humidified air-oxygen mixture.

FIG. 7 shows an illustrative process 700 for achieving a heated and humidified air-oxygen mixture for delivery to a patient. The process 700 can be performed using either of the systems 100 or 200 described herein. It will be understood by one of ordinary skill in the art that, in addition to the steps shown in FIG. 7, the heated and humidified air-oxygen mixture may be delivered to a patient by any suitable means.

In step 702, air is passed form an air compressor unit 150 to a compressed air passage 158. The air passed from the air compressor unit 150 has a first pressure 159 which may be determined by an input from the controls of the system 100 or 200. The air compressor unit 150 may draw air 140 into the air compressor unit 150 through an air inlet 142 before compressing the air 152 and expelling it from the air outlet 156 into a compressed air passage 158. The air may be ambient room air. Though the air inlet 142 is depicted as drawing ambient room air, in some implementations the system 100, 200 may also allow attachment of high or low pressure external air and oxygen sources.

In step 704, oxygen is passed from an oxygen concentrator unit 160 to an oxygen passage 168. The oxygen concentrator unit 160 may draw air 140 into the concentrator unit 160 through an air inlet 142. The air may be ambient room air. The oxygen concentrator unit 160 concentrates the oxygen in the air 140 and expels concentrated oxygen 162 through a concentrated oxygen outlet 166 and into the oxygen passage 168. The concentrated oxygen 162 has a second pressure 169.

In step 706, the oxygen from the oxygen concentrator unit 160 and the compressed air from the air compressor unit 150 are mixed at the junction 170. The concentrated oxygen 162 meets the compressed air 152 at the junction 170 of the compressed air passage 158 and the oxygen passage 168. The compressed air 152 has a first pressure 159 which is about equal to the second pressure 169 of the concentrated oxygen 162. The compressed air 152 and the concentrated oxygen 162 mix without one gas overcoming the other due to the matched pressure. The mixing of the compressed air 152 and the concentrated oxygen 162 at the junction 170 may be enhanced by the presence of a manifold or other director to direct the flows of the compressed air 152 and concentrated oxygen 162 for a smooth blending.

In step 708, the air 140 and oxygen 162, which have been mixed into an air-oxygen breathing gas mixture 174, are passed through the vapor transfer system 120. The vapor transfer system 120 includes a liquid reservoir 134 and means to heat the liquid 138. The heated liquid and vapor are passed through a liquid passage 130. The air-oxygen breathing gas mixture 174 is directed through a gas passage 126 which is separated from the liquid passage 130 by a membrane 132 which allows the transfer of vapor to the air-oxygen breathing gas mixture 174 in order to heat and humidify the air-oxygen breathing gas mixture 174. The humidity and heat of the air and oxygen mixture may be controlled. The humidified and heated air-oxygen breathing gas mixture 174 is then passed out of the system for delivery to a patient via a nasal cannula 290 or any other suitable means.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. An apparatus for delivering a heated and humidified mixture of oxygen and air, the apparatus comprising:
   a vapor transfer system having a housing, a gas inlet, a gas outlet, a liquid inlet, a liquid outlet, a gas passage coupling the gas inlet to the gas outlet, a liquid passage coupling the liquid inlet to the liquid outlet, and a membrane separating the gas passage and the liquid passage, wherein the membrane is positioned to transfer vapor from the liquid passage to the gas passage;
   a liquid supply coupled to the liquid inlet and having a heater that heats liquid of the liquid supply;
   an air compressor enclosed in the housing and configured to supply air at a first pressure to the gas inlet;
   an oxygen concentrator enclosed in the housing and configured to output oxygen at a second pressure to the gas inlet, wherein the oxygen concentrator and the air compressor are in fluid communication;
   a control mechanism operatively coupled to the air compressor and the oxygen concentrator and configured to control the air compressor and the oxygen concentrator such that the first pressure and the second pressure are about equal; and
   a junction configured to receive air from the air compressor and oxygen from the oxygen concentrator, the junction being in fluid communication with the gas inlet.

2. The apparatus of claim 1 wherein the first pressure and the second pressure are equal within 10%.

3. The apparatus of claim 1, wherein the first pressure and the second pressure are equal within 5%.

4. The apparatus of claim 1, wherein the first pressure and the second pressure are about 6-11 psi.

5. The apparatus of claim 1, wherein the gas outlet is in fluid communication with a first elongated lumen and a second elongated lumen, wherein the first elongated lumen is coupled to a first end of a nasal cannula and the second elongated lumen is coupled to a second end of a nasal cannula, wherein a first flow of gas from the first elongated lumen and a second flow of gas from the second elongated lumen are directed through a first and second nasal prong.

6. The apparatus of claim 5, wherein the first flow of gas through the first elongated lumen and the second flow of gas through the second elongated lumen are not in fluid communication throughout the nasal cannula.

7. The apparatus of claim 5, wherein the first flow of gas through the first elongated lumen and the second flow of gas through the second elongated lumen are in fluid communication at the first and second nasal prong.

8. The apparatus of claim 5, wherein the nasal cannula defines a constant diameter flow path.

9. The apparatus of claim 5, wherein an inner diameter of the first elongated lumen and an inner diameter of the second elongated lumen are about equal to ¼".

10. The apparatus of claim 5 wherein the flow rate through the first elongated lumen and the second elongated lumen is 40 lpm or greater.

11. The apparatus of claim 5, wherein the first elongated lumen and the second elongated lumen each has a length of about 1.8 meters and wherein the first elongated lumen and the second elongated lumen each provides a gas from the gas outlet at a range of flow rates of about 5-40 lpm.

12. The apparatus of claim 5, wherein the first elongated lumen and the second elongated lumen each has a length of about 10 m.

13. The apparatus of claim 12, wherein the first elongated lumen and the second elongated lumen provide a gas from the gas outlet at a range of flow rates of about 0.25-10 lpm.

14. The apparatus of claim 5, wherein the first and second flow of gas maintain a temperature within +/−5 degrees Celsius from a set temperature across a range of flow rates from 5-40 lpm.

15. The apparatus of claim 5, wherein the flow of gas exits the gas outlet with a humidity within the range of 26-56 mg/L.

16. The apparatus of claim 1, further comprising a base unit that releasably engages the vapor transfer unit to enable reuse of the base unit and selective disposal of the vapor transfer unit, the liquid passage coupled to the base unit for liquid flow between the base unit and the vapor transfer unit when the vapor transfer unit is received by the base unit.

17. The apparatus of claim 1, wherein the membrane comprises a plurality of hollow fiber tubes.

18. The apparatus of claim 1, wherein the gas passage is enveloped by the liquid passage.

19. The apparatus of claim 1, wherein the liquid passage is enveloped by the gas passage.

20. The apparatus of claim 1, wherein the apparatus operates at a sound level of about 55 dB or lower.

21. The apparatus of claim 1, wherein the control mechanism is configured to automatically control the air compressor and the oxygen concentrator such that the first pressure and the second pressure are about equal.

22. The apparatus of claim 1, wherein the control mechanism is configured to set at least one of the first pressure or the second pressure in response to a user input.

23. The apparatus of claim 1, wherein the control mechanism is operatively coupled to the heater and the vapor transfer system, and wherein the control mechanism is configured to toggle between a first mode and a second mode, the first mode being delivery of a heated and humidified mixture of air and oxygen, the second mode being delivery of a humidified mixture of air and oxygen that is not heated.

* * * * *